United States Patent
Tamez-Peña et al.

(10) Patent No.: US 6,998,841 B1
(45) Date of Patent: Feb. 14, 2006

(54) METHOD AND SYSTEM WHICH FORMS AN ISOTROPIC, HIGH-RESOLUTION, THREE-DIMENSIONAL DIAGNOSTIC IMAGE OF A SUBJECT FROM TWO-DIMENSIONAL IMAGE DATA SCANS

(75) Inventors: José Tamez-Peña, Rochester, NY (US); Saara Marjatta Sofia Totterman, Rochester, NY (US); Kevin J. Parker, Rochester, NY (US)

(73) Assignee: Virtualscopics, LLC, Rochester, NY (US)

( * ) Notice: Subject to any disclaimer, the term of this patent is extended or adjusted under 35 U.S.C. 154(b) by 0 days.

(21) Appl. No.: 09/540,524

(22) Filed: Mar. 31, 2000

(51) Int. Cl.
- G01R 33/20 (2006.01)
- G01V 3/00 (2006.01)
- A61B 5/055 (2006.01)
- G06K 9/00 (2006.01)

(52) U.S. Cl. .................. 324/302; 600/410; 324/307; 382/131

(58) Field of Classification Search ......... 324/300–322; 378/4; 382/128–132; 128/920
See application file for complete search history.

(56) References Cited

U.S. PATENT DOCUMENTS

| | | | |
|---|---|---|---|
| 5,133,357 A | 7/1992 | Dumoulin et al. ........... 600/413 | |
| 5,245,282 A * | 9/1993 | Mugler et al. ............... 324/309 | |
| 5,305,204 A | 4/1994 | Ohhashi ..................... 382/131 | |
| 5,374,889 A | 12/1994 | Leach et al. | |
| 5,412,563 A | 5/1995 | Cline et al. | |
| 5,442,733 A | 8/1995 | Kaufman et al. | |
| 5,446,384 A | 8/1995 | Dumoulin | |
| 5,633,951 A | 5/1997 | Moshfeghi | |
| 5,709,208 A | 1/1998 | Posse et al. ................. 600/410 | |
| 5,749,834 A | 5/1998 | Hushek | |
| 5,786,692 A | 7/1998 | Maier et al. ................. 324/307 | |
| 5,818,231 A | 10/1998 | Smith | |
| 5,825,909 A | 10/1998 | Jang | |
| 5,839,440 A | 11/1998 | Liou et al. | |
| 5,891,030 A | 4/1999 | Johnson et al. | |
| 5,926,568 A | 7/1999 | Chaney et al. | |
| 5,928,146 A | 7/1999 | Itagaki et al. ............... 600/410 | |
| 6,031,935 A | 2/2000 | Kimmel | |
| 6,178,220 B1 | 1/2001 | Freundlich et al. ............ 378/4 | |
| 6,239,597 B1 * | 5/2001 | McKinnon ................... 324/307 | |
| 6,480,565 B1 * | 11/2002 | Ning ............................ 378/37 | |
| 6,526,305 B1 * | 2/2003 | Mori ........................... 600/410 | |
| 2003/0135103 A1 * | 7/2003 | Mistretta ..................... 600/410 | |

FOREIGN PATENT DOCUMENTS

EP    WO 98/24063    6/1998

OTHER PUBLICATIONS

Higashi M "FASE" (fast advanced spin echo) Nippon rinsho. Japanese journal of clinical medicine (Japan) Nov. 1998, 56 (11) p2783–91, ISSN 0047–1852.*

(Continued)

Primary Examiner—Diego Gutierrez
Assistant Examiner—Tiffany A. Fetzner
(74) Attorney, Agent, or Firm—Blank Rome LLP

(57) ABSTRACT

MRI scans typically have higher resolution within a slice than between slices. To improve the resolution, two MRI scans are taken in different, preferably orthogonal, directions. The scans are registered by maximizing a correlation between their gradients and then fused to form a high-resolution image. Multiple receiving coils can be used. When the images are multispectral, the number of spectral bands is reduced by transformation of the spectral bands in order of image contrast and using the transformed spectral bands with the highest contrast.

18 Claims, 7 Drawing Sheets

OTHER PUBLICATIONS

Mellin, A.F. et al, "Three dimensional magnetic resonance microangiography of rat neurovasculature" magnetic resonance in medicine vol. 32, No. 2, pp. 199–205 1994.*

Henson M M; et al., "Imaging the cochlea by magnetic resonance microscopy" Hearing research (Netherlands) May 1994, 75 (1–2) pp. 75–80, ISSN 0378–5955.*

Catherine Westbrook and Carolyn Kaut textbook "MRI in Practice Second Edition" Blackwell Science, Inc., pp. 47–57 and pp. 101–103 1998.*

Bushberg et al., textbook "The Essential Physics of Medical Imaging", Williams and Wilkins Philadelphia pp. 325–327; 332–333; 336–339 1994.*

José G. Tamez Peña, et al., Automatic Statistical Segmentation of Medical Volumetric Images, IEEE Computer Vision and Pattern Recognition 98, pp 1–7.

Jagath C. Rajapakse, et al., Statistical Approach to Segmentation of Single–Channel Cerebral MR Images, IEEE Transactions on medical imaging, vol. 16, No. 2, pp. 176–186, 1997.

W.M. Wells III et al., "Adaptive Segmentation of MRI Data", IEEE Transactions on Medical Imaging, pp. 429–440, 1996.

M.W. Hansen, et al., "Relaxation Methods for Supervised Image Segmentation", IEEE Trans. Patt. Anal. Mach. Intel., vol. 19, pp. 949–962, 1997.

E.A. Ashton, et al., Segmentation and Feature Extraction Techniques, with Applications to MRI Head Studies, IEEE Transactions on Medical Imaging, vol. 16, pp. 365–371, 1997.

W.E. Higgins, et al., "Extraction of Left–Ventricular Chamber from 3–D CT Images of the Heart", Transactions on Medical Imaging, vol. 9, No. 4, pp. 384–394, 1990.

* cited by examiner

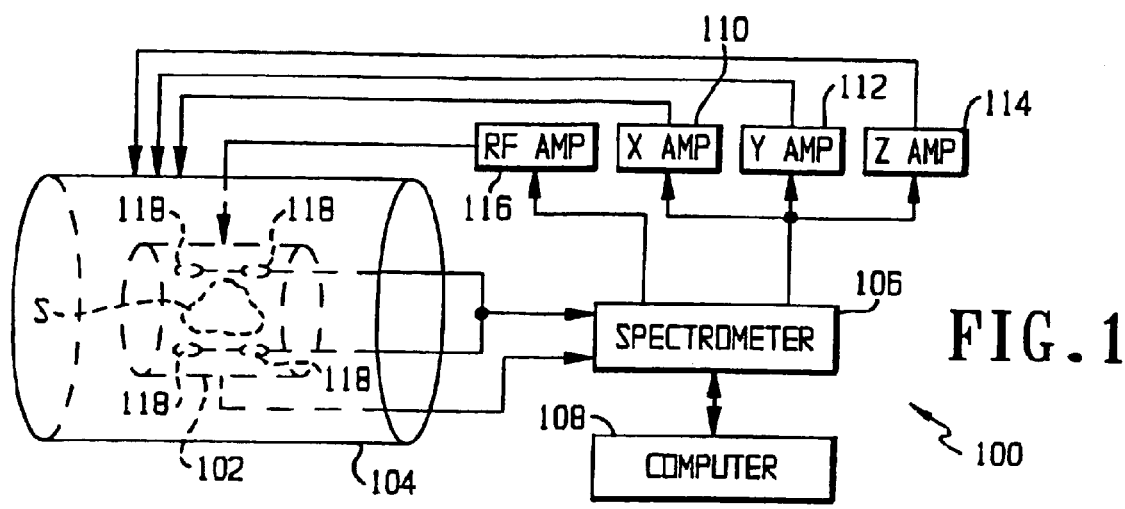
FIG.1
FIG.2
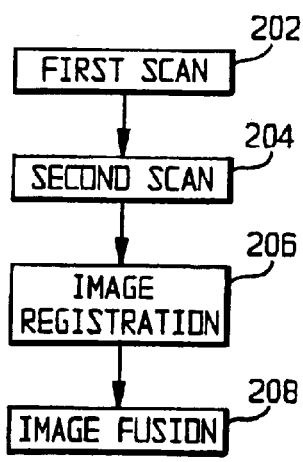
FIG.3
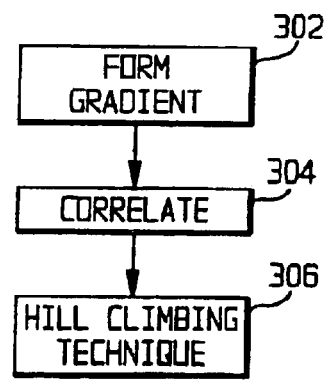
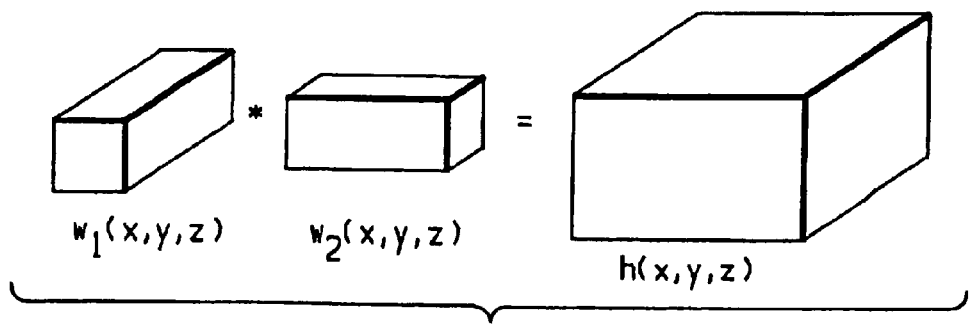
FIG.4

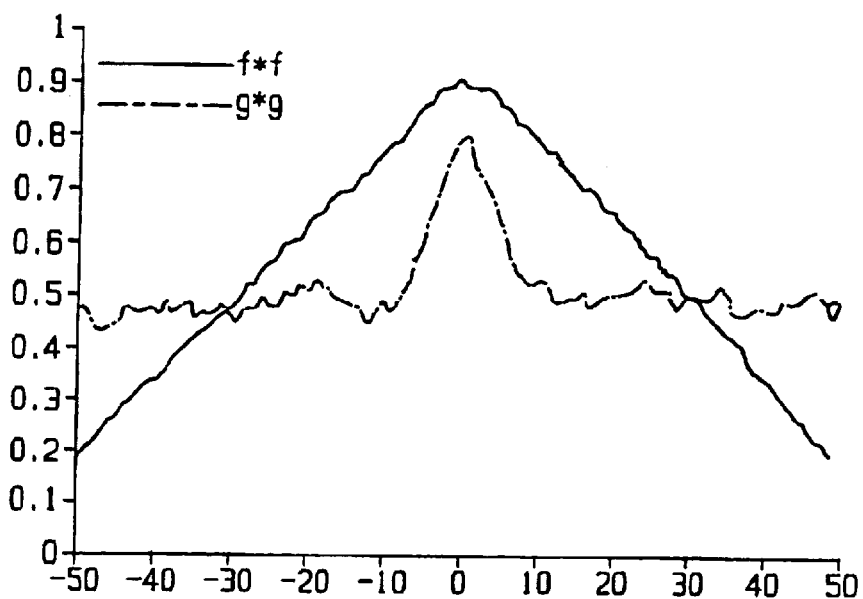
FIG.5C
FIG.6A
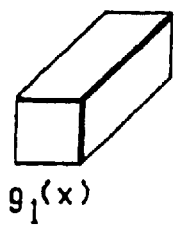
$g_1(x)$
FIG.6B
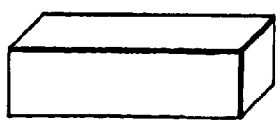
$g_2(x)$
FIG.6C
| $g_2(y+3)$ | | | | $g(x+3, y+3)$ |
| $g_2(y+2)$ | | | | |
| $g_2(y+1)$ | | | | |
| $g_2(y)$ | $g(x,y)$ ? | | | |
| | $g_1(x)$ | $g_1(x+1)$ | $g_1(x+2)$ | $g_1(x+3)$ |
KNOWN 400
METHOD AND SYSTEM WHICH FORMS AN ISOTROPIC, HIGH-RESOLUTION, THREE-DIMENSIONAL DIAGNOSTIC IMAGE OF A SUBJECT FROM TWO-DIMENSIONAL IMAGE DATA SCANS

BACKGROUND OF THE INVENTION

1. Field of the Invention

The present invention is directed to a system and method for improving the resolution and tissue contrast in MRI.

2. Description of Related Art

The best current source of raw image data for observation of a complex soft tissue and bone structure is magnetic resonance imaging (MRI). MRI involves the transmission of RF signals of predetermined frequency (e.g., approximately 15 MHZ in some machines, the frequency depending upon the magnitude of magnetic fields employed and the magnetogyric ratio of the atoms to be imaged). Typically, exciting pulses of RF energy of a specific frequency are transmitted via an RF coil structure into an object to be imaged. A short time later, radio-frequency NMR responses are received via the same or a similar RF coil structure. Imaging information is derived from such RF responses.

In MRI, a common imaging technique is the formation of images of selected planes, or slices, of the subject being imaged. Typically the subject is located in the static magnetic field with the physical region of the slice at the geometric center of the gradient field. Generally, each gradient will exhibit an increasing field strength on one side of the field center, and a decreasing field strength on the other side, both variations progressing in the direction of the particular gradient. The field strength at the field center will thus correspond to a nominal Larmor frequency for the MRI system, usually equal to that of the static magnetic field. The specific component of a gradient which causes the desired slice to be excited is called the slice selection gradient. Multiple slices are taken by adjusting the slice selection gradient.

However, MRI often introduces the following technical challenges. Many of the anatomical structures to be visualized require high resolution and present low contrast, since, for example, many of the musculoskeletal structures to be imaged are small and intricate. MRI involves the use of local field coils to generate an electromagnetic field; such local field coils form a non-uniform illumination field. MRI images can also be noisy.

In particular, MRI has the following limitations in resolution and tissue contrast. Although current MRI machines can achieve relatively high intra-plane resolution, the inter-slice resolution is not so good as the intra-plane resolution; also, the inter-slice resolution is limited by the ability of the system to stimulate a single spatial slice or section. Although tissue contrast can be adjusted by selecting the right pulse sequence, analysis of a single pulse sequence is not enough to differentiate among adjacent similar tissues. In other words, the resolution is typically poor in the out-of-plane dimension, and the contrast is typically low between soft tissue structures.

SUMMARY OF THE INVENTION

It will be readily apparent from the foregoing that a need exists in the art to overcome the above-noted limitations of conventional MRI.

Therefore, it is an object of the present invention to increase inter-slice resolution.

It is another object of the present invention to improve tissue contrast.

It is still another object of the present invention to improve inter-slice resolution and tissue contrast simultaneously.

It is yet another object to provide a simple technique for image registration.

To achieve the above and other objects, the present invention is directed to a system and method for creating high-resolution MRI volumes and also high-resolution, multi-spectral MRI volumes. At least one additional scan is obtained in an orthogonal direction. Then, through a data fusion technique, the information from an original scan and an orthogonal scan are combined, so as to produce a high-resolution, 3D volume. In addition, one may use a different pulse sequence in the original orientation or in an orthogonal orientation, and a data fusion technique can be applied to register the information and then visualize a high-resolution, multi- spectral volume.

BRIEF DESCRIPTION OF THE DRAWINGS

A preferred embodiment will be set forth in detail with reference to the drawings, in which:

FIG. 1 shows a block diagram of an MRI system according to the preferred embodiment;

FIGS. 2 and 3 show flow charts showing steps performed in registering and fusing two images;

FIG. 4 shows a blurring effect caused by the correlation of the two images;

FIGS. 5A–5C show a typical signal, its gradient and a comparison of the autocorrelations of the signal and its gradient, respectively;

FIGS. 6A and 6B show two voxels scanned in orthogonal directions;

FIG. 6C shows the problem of deriving high-resolution information from the voxels of FIGS. 6A and 6B;

DETAILED DESCRIPTION OF THE PREFERRED EMBODIMENT

Figure 5A:
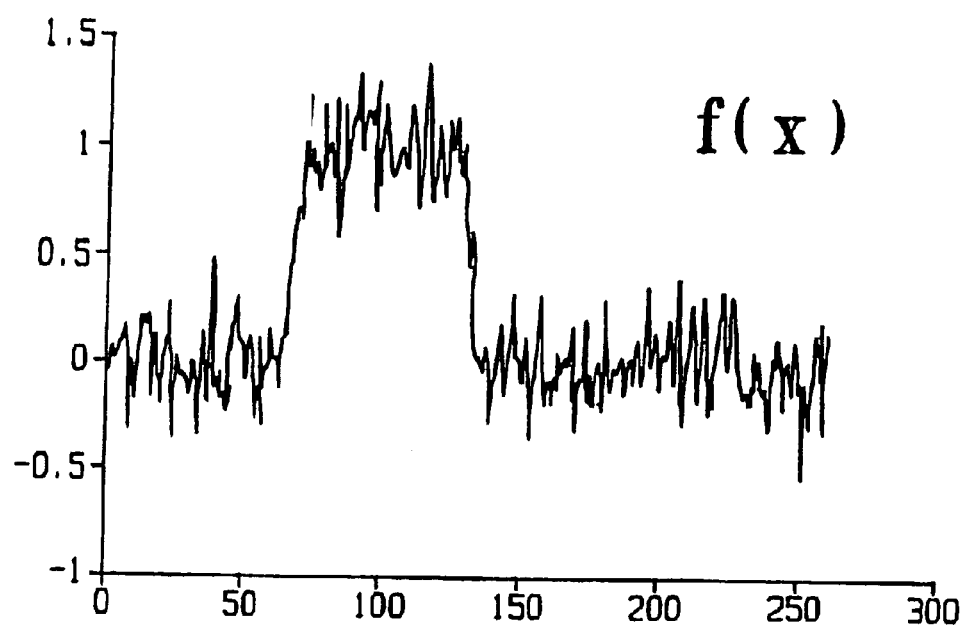

A preferred embodiment of the present invention will now be set forth in detail with reference to the drawings.

FIG. 1 shows a block diagram of an MRI system 100 on which the present invention can be implemented. The system 100 uses an RF coil 102 and a gradient coil 104 to apply the required RF and gradient fields to the subject S. A spectrometer 106, acting under the control of a computer 108, generates gradient signals which are amplified by an X amplifier 110, a Y amplifier 112 and a Z amplifier 114 and applied to the gradient coil 104 to produce the gradient fields. The spectrometer 106 also generates RF signals which are amplified by an RF amplifier 116 and applied to the RF coil 102 to produce the RF fields. The free induction decay radiation from the sample S is detected by the RF coil 102 or by one or more local receiving coils 118 and applied to the spectrometer 106, where it is converted into a signal which the computer 108 can analyze.

The computer 108 should be sufficiently powerful to run a mathematical analysis package such as AVS, a product of Advanced Visualization Systems of Waltham, Mass., U.S.A. Examples are the Apple Power Macintosh and any IBM-compatible microcomputer capable of running Windows 95, 98 or NT. The significance of the local receiving coils 118, and particularly of the number used, will be explained in detail below. The other components of the system 100 will be familiar to those skilled in the art and will therefore not be described in detail here.

The various techniques to enhance the images will now be described in detail.

Inter-Slice Resolution

The inter-slice resolution problem is solved by using two volumetric data sets where scanning directions are orthogonal to each other, and fusing them in a single high-resolution image. FIG. 2 shows an overview of the process. First, in step 202, a first scan of the subject is taken. In step 204, a second scan of the subject is taken in a direction orthogonal to that of the first scan. Third, in step 206, the images are registered. Finally, in step 208, the images are fused. FIG. 3 shows the steps involved in image registration. In step 302, gradients of the image data are formed. In step 304, the gradients are correlated. In step 306, the correlation is maximized through a hill-climbing technique.

Although the fusion of the two volumes seems to be trivial, two issues have to be taken into account: 1) the registration among volumes scanned at different time (step 206) and 2) the overlapping of sampling voxel volumes (step 208). Those issues are handled in ways which will now be described.

Image Registration (Step 206)

The goal of image registration is to create a high-resolution 3D image from the fusion of the two data sets. Therefore, the registration of both volumes has to be as accurate as the in-plane resolution. The preferred embodiment provides a very simple technique to register two very similar orthogonal MRI images. The registration is done by assuming a simple translation model and neglecting the rotation among the two volumes, thus providing a fair model for small and involuntary human motion between scans.

An unsupervised registration algorithm finds the point (x, y, z) where the correlation between the two data sets is maximum. The Schwartz inequality identifies that point as the point where they match. Given two functions $u(x, y, z)$ and $v(x, y, z)$, the correlation is given by:

$$r(x, y, z) = u(x, y, z) * v(x, y, z)$$

$$= \int\int\int u(\alpha, \beta, \gamma) v(x+\alpha, y+\beta, z+\gamma) d\alpha d\beta d\gamma.$$

If $u(x, y, z)$ is just a displaced version of $v(x, y, z)$, or in other words, $u(x, y, z) = v(x+\Delta x, y+\Delta y, z+\Delta z)$, then the maximum is at $(-\Delta x, -\Delta y, -\Delta z)$, the displacement between the functions.

In MRI, every voxel in the magnetic resonance image observes the average magnetization of an ensemble of protons in a small volume. The voxel can therefore be modeled as the correlation of the continuous image by a small 3D window. Let $g_1(x, y, z)$ and $g_2(x, y, z)$ be the sampled volumes at two orthogonal directions, which are given by:

$$g_1(x,y,z) = f(x,y,z) * w_1(x,y,z) * \Pi(x,y,z)$$

$$g_2(x,y,z) = f(x+\Delta x, y+\Delta y, z+\Delta z) * w_2(x,y,z) * \Pi(x,y,z)$$

where $w_1(x, y, z)$ and $w_2(x, y, z)$ are the 3D windows for the two orthogonal scanning directions, $(\Delta x, \Delta y, \Delta z)$ is a small displacement, and $\Pi(x, y, z)$ is the sampling function. Therefore, the correlation of the two sampled volumes is $$r(x,y,z) = g_1(x,y,z) * g_2(x,y,z)$$

$$= f(x+\Delta x, y+\Delta y, z+\Delta z) * f(x,y,z) * w_2(x,y,z) * \Pi(x,y,z).$$

That is just a blurred version of the original correlation; the exact location of the maxima is shaped by the blurring function $h(x, y, z) = w_1(x, y, z) * w_2(x, y, z)$. That is, the correlation is distorted by the function $h(x, y, z)$. FIG. 4 shows an idealized window function for $w_1(x, y, z)$ and $w_2(x, y, z)$ and its corresponding supporting region of the blurring function, $h(x, y, z)$.

Finding the displacement using the above procedure works fine for noise-free data, but noise makes the search more difficult. Let $g_1(x, y, z) = (f(x, y, z) + n_1(x, y, z)) * w_1(x, y, z)$ and $g_2(x, y, z) = (f(x+\Delta x, y+\Delta y, z+\Delta z) + n_2(x, y, z)) * w_2(x, y, z)$ be the corresponding noisy volumes, where $n_1(x, y, z)$ and $n_2(x, y, z)$ are two uncorrelated noise sources. Thus, the correlation of $g_1$ and $g_2$ is given by $$r(x,y,z) = g_1(x,y,z) * g_2(x,y,z)$$

$$= [f(x+\Delta x, y+\Delta y, z+\Delta z) * f(x,y,z) +$$

$$f(x+\Delta x, y+\Delta y, z+\Delta z) * n_1(x,y,z) +$$

$$f(x,y,z) * n_2(x,y,z)] * h(x,y,z) * \Pi(x,y,z),$$

and the maximum is no longer guaranteed to be given by the displacement, especially for functions with smooth autocorrelation functions like standard MRI. The smooth autocorrelation functions make the error a function of the noise power. Autocorrelation functions whose shapes are closer to a Dirac delta function $\delta(x, y, z)$ are less sensitive to noise, which is the reason why many registration algorithms work with edges. The autocorrelation function of the gradient magnitude of standard MRI is closer to a Dirac delta function. Therefore, the registration of the gradient is less sensitive to noise.

Figure 5B:
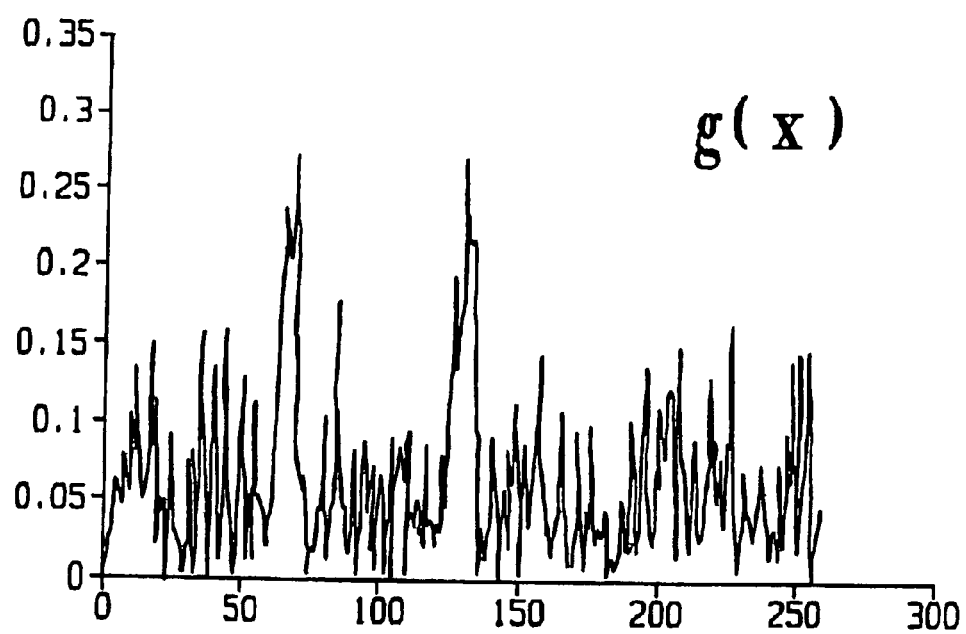

FIGS. 5A–5C shows a 1D example of the effect of the derivative on the autocorrelation function of a band-limited signal. FIG. 5A shows an original signal $f(x)$. FIG. 5B shows a smooth estimate of the magnitude of the derivative, namely, $$g(x) = |f(x) * [-1 \quad -1 \quad 0 \quad 0 \quad 1 \quad 1]|$$

FIG. 5C shows autocorrelations; the dashed curve represents $f*f$, while the curve shown in crosses represents $g*g$. For that example, a smooth derivative operator is used to reduce the noise level.

For the above reasons, the automatic registration is based on finding the maximum on the correlation among the magnitude gradient of the two magnetic resonance images:

$$(\Delta x, \Delta y, \Delta z) =$$

$$\text{Arg} \max_{(\Delta x, \Delta y, \Delta z)} \int \int \int \|\nabla g_1(\alpha, \beta, \gamma)\| \|\nabla g_2(\Delta x + \alpha, \Delta y + \beta, \Delta z + \gamma)\| d\alpha d\beta d\gamma.$$

In sampled images the gradient $\nabla$ can be approximated by finite differences:

$$\|\nabla g(x, y, z)\| = \sqrt{d_x(x, y, z)^2 + d_y(x, y, z)^2 + d_z(x, y, z)^2},$$

where $$d_x(x, y, z) = \frac{l(x, y, z) * g(x + \delta x, y, z) - l(x, y, z) * g(x - \delta x, y, z)}{2\delta x},$$

$$d_y(x, y, z) = \frac{l(x, y, z) * g(x, y + \delta y, z) - l(x, y, z) * g(x, y - \delta y, z)}{2\delta y},$$

$$d_z(x, y, z) = \frac{l(x, y, z) * g(x, y, z + \delta z) - l(x, y, z) * g(x, y, z - \delta z)}{2\delta z},$$

where $\delta x$, $\delta y$, $\delta z$ are the sampling rates, and $l(x, y, z)$ is a low pass filter used to remove noise from the images and to compensate the differences between in-slice sampling and inter-slice sampling.

The maximization can be done using any standard maximization technique. The preferred embodiment uses a simple hill-climbing technique because of the small displacements. The hill-climbing technique evaluates the correlation at the six orthogonal directions: up, down, left, right, front and back. The direction that has the biggest value is chosen as the next position. That simple technique works well for the registration of two orthogonal data sets, as the one expects for involuntary motion during scans.

To avoid being trapped in local maxima and to speed up the process, a multi-resolution approach can be used. That multi-resolution approach selects the hill-climbing step as half the size of the previous step. Five different resolutions are used. The coarsest resolution selected is twice the in-plane resolution of the system, and the smallest size is just 25 percent of the in-plane resolution.

Even with a very simple optimization approach, the computation of the correlation of the whole data set can be time consuming; therefore, the registration of two images can take time. To speed up the correlation of the two data sets, just a small subsample of the points with very high gradient are selected for use in the correlation process.

Some images suffer from a small rotation. In that case, the algorithm is extended to search for the image rotation. The same hill-climbing technique is used to find the rotation between images; but instead of doing the search in a three-dimensional space, the algorithm has to look at a six-dimensional space. That search space includes the three displacements and three rotations along each axis. At each step the rotation matrix is updated and used to compensate for the small rotation between images.

Image Fusion (Step 208)

Once the two images are registered, an isotropic high resolution image is created from them. Due to the different shape between voxel sampling volumes ($w_2(x, y, z)$ and $w_1(x, y, z)$), one has to be careful when estimating every high resolution voxel value from the input data. Assume that the first image has been scanned in the x-direction and the second has been scanned in the y-direction. Therefore, there is high-resolution information in the z-direction in both images.

FIGS. 6A and 6B show the voxel shapes of the two input images, where the in-slice resolution is equal, and the inter-slice resolution is four times lower. Given that configuration, the problem of filling the high-resolution volume is a 2D problem. In a single 4×4-voxel window of the high resolution image, as seen in FIG. 6C, then for every 16 high-resolution voxels there are only 8 known low-resolution voxels; therefore, that is an ill posed problem.

To address that problem, assume that every high-resolution voxel is just a linear combination of the two low-resolution functions:

$$g(x,y,z) = h_1(x/s_d, y, z) + h_2(x, y/s_d, z),$$

where $h_1$, $h_2$ are two functions which are back projected in such a way that $$g_1(x/s_d, y, z) = \sum_{\forall x \in w_1} g(x, y, z),$$

$$g_2(x, y/s_d, z) = \sum_{\forall y \in w_2} g(x, y, z).$$

That represents a linear system with the same number of knowns as unknowns. The known values are the observed image voxels, while the values to back-project which match the observation are estimated. Noise and inhomogeneous sampling make the problem a little bit harder; but that linear system can efficiently be solved using projection on convex sets (POCS). Although, in theory, all the components have to be orthogonally projected, it can be shown that the following projecting scheme also works:

$$h_1^{k+1}(x/s_d, y, z) = h_1^k(x/s_d, y, z) - \alpha \frac{\left(n h_1^k(x/s_d, y, z) + \sum_{\forall x \in w_1} h_2^k(x, y/s_d, z) - g_1(x/s_d, y, z)\right) n}{n^2 + m},$$

$$h_2^{k+1}(x, y/s_d, z) = h_2^k(x, y/s_d, z) - \alpha \frac{\left(m h_2^k(x, y/s_d, z) + \sum_{\forall y \in w_2} h_1^k(x/s_d, y, z) - g_1(x, y/s_d, z)\right) m}{n + m^2},$$

where $0 < \alpha < 1$, n=the window size of $w_1$, m=the window size of $w_2$, $h_1^0(x, y, z) = g(x, y, z)$ and $h_2^0(x, y, z) = g_2(x, y, z)$ are the initial guesses for the estimation of back-projected functions. The advantage of that approach over standard orthogonal projection is that is equations are simpler and that they can be implemented efficiently on a computer.

Experimental Data

Some experimental data produced by the above technique will now be described.

Figure 7A:
FIGS. 7A–7I show comparisons between the individual scans and the fused image.
Figure 7B:
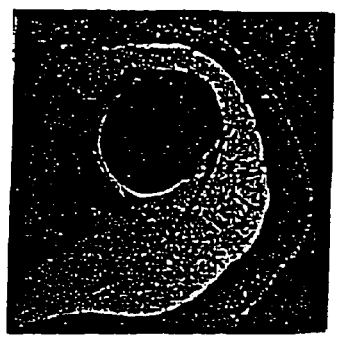
Figure 7C:
Figure 7D:
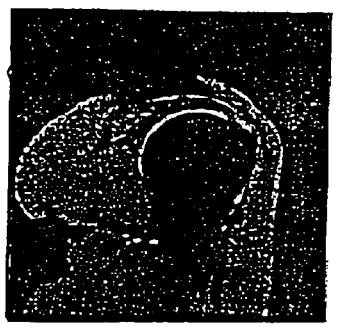
Figure 7E:
Figure 7F:
Figure 7G:
Figure 7H:
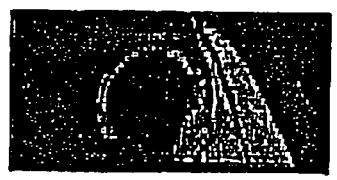
Figure 7I:

FIGS. 7A, 7B and 7C respectively show the original MRI sagittal scan, the original MRI axial scan and the fused image of a human shoulder seen along an axial view. FIGS. 7D, 7E and 7F show the same, except seen along a sagittal view. FIGS. 7G, 7H and 7I show the same, except seen along a coronal view. In all three cases, the image is noticeably improved.

Figure 8A:
FIGS. 8A–8I show a comparison among simple fusion without registration, simple fusion after registration and complete fusion.
Figure 8B:
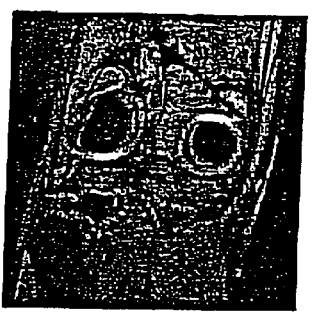
Figure 8C:
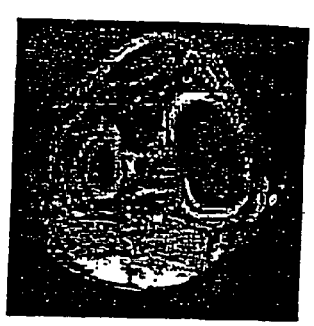
Figure 8D:
Figure 8E:
Figure 8F:
Figure 8G:
Figure 8H:
Figure 8I:
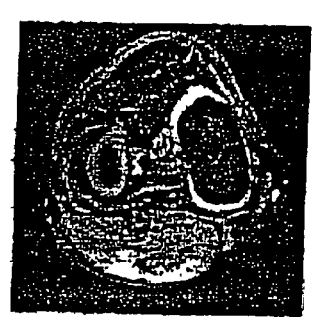

FIGS. 8A, 8B and 8C show axial, sagittal and coronal slices, respectively, of simple fusion without registration. FIGS. 8D, 8E and 8F show the same slices with simple fusion after registration. FIGS. 8G, 8H and 8I show the same slices with complete image fusion. The simple fusion is $g(x, y, z) = 0.5 g_1(x, y, z) + 0.5 g_2(x, y, z)$, and the complete fusion is g(x, y, z)=h₁(x, y, z)+h₂(x, y, z), wherein h₁ and h₂ are the two functions which minimize the reconstruction error.

Figure 9A:
FIGS. 9A–9I show fusion of orthogonal images without correlation.
Figure 9B:
Figure 9C:
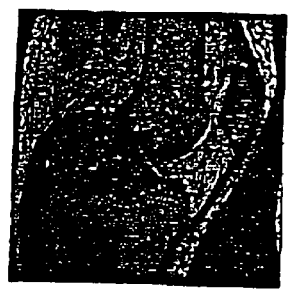
Figure 9D:
Figure 9E:
Figure 9F:
Figure 9G:
Figure 9H:
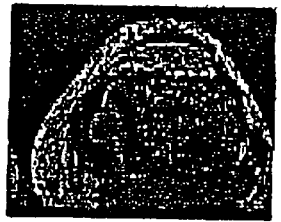
Figure 9I:
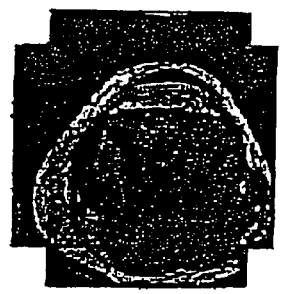

FIGS. 9A–9I show fusion of orthogonal images without correlation. FIGS. 9A, 9B and 9C show axial views of the original MRI sagittal scan, the original axial scan and the fused image, respectively, for an axial view. FIGS. 9D, 9E and 9F show the same for a sagittal view. FIGS. 9G, 9H and 9I show the same for a coronal view.

Multiple Local Coil Receivers and Multispectral Imaging

Good signal-to-noise ratio is very important for an unsupervised segmentation algorithm. Even more important is the contrast-to-noise ratio among neighboring tissues. When local receiving coils are used, the signal from points far from the coil location is weak; therefore, contrast among tissues located far from the receiving coil is low. Some researchers have proposed several software alternatives to correct this signal fading, but this will increase the noise levels as well. Thus, it will not solve the problem. The preferred embodiment uses two or more receiving coils, which will improve the signal reception at far locations.

Figure 10A:
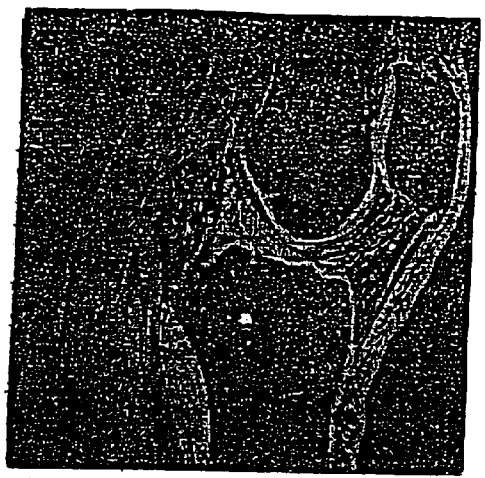
FIGS. 10A and 10B show images taken with three and four local receiver coils, respectively.
Figure 10B:
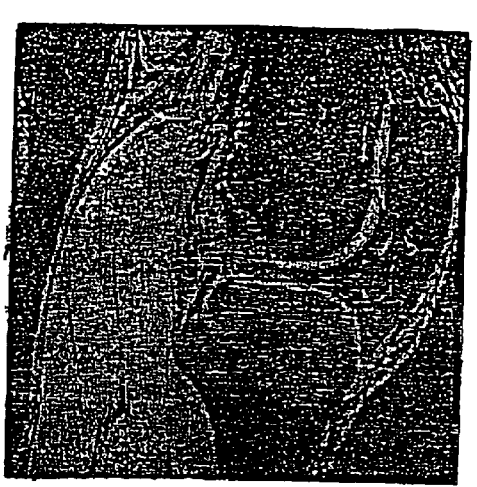

FIGS. 10A and 10B show the advantage of using multiple coils. FIG. 10A shows an MRI image of a knee using three surface coils. FIG. 10B shows an MRI image of the same knee using four surface coils.

Multispectral images will now be considered. Such images can be analogized to multispectral optical images, in which, for example, red, blue and green images are combined to create a single color image.

Figure 11A:
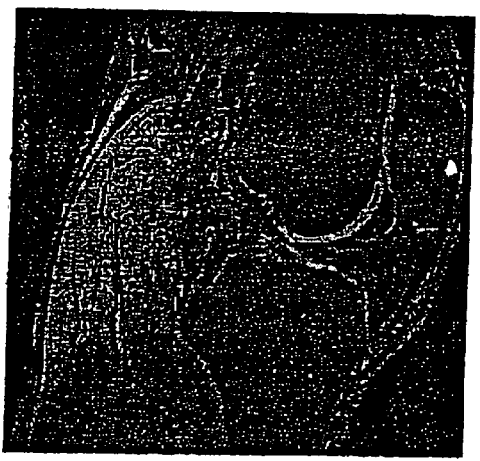
FIGS. 11A and 11B show a two-band spectral image of a knee.
Figure 11B:
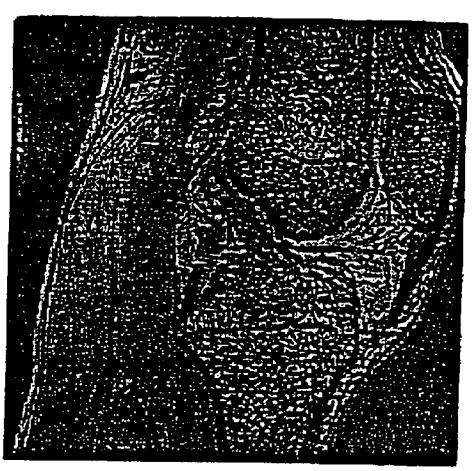

FIGS. 11A and 11B show a two-band spectral image of a knee. FIG. 11A shows a cross section of a fat suppression MRI scan of the knee, where fat, and bone tissues have almost the same low density, cartilage has a very high density, and muscle tissue has a medium density. FIG. 11B shows the same knee, but now, muscle tissue and cartilage have the same density, making them very hard to differentiate. Those images clearly show the advantage of the multispectral image approach in describing the anatomy.

The analysis of a multispectral image is more complex than that of a single-spectrum image. One way to simplify the analysis is to reduce the number of bands by transforming an N-band multispectral image in such a way that passes the most relevant image into an (N-n)-band image. The transform that minimizes the square error between the (N-n)-band image and the N-band image is the discrete Karhuen-Loeve (K-L) transform. The resulting individual images from the transformed spectral image after applying the K-L transform are typically known as the principal components of the image.

Let the voxel x be an N-dimensional vector whose elements are the voxel density from each individual pulse sequence. Then the vector mean value of the image is defined as $$m_x = E[x] = \frac{1}{M}\sum_{k=1}^{M} x_k,$$

and the covariance matrix is defined as $$C_x = E[(x-m_x)(x-m_x)^2] = \frac{1}{M}\sum_{k=1}^{M} x_k x_k^T - m_k m_k^T,$$

where M is the number of voxels in the image.

Figure 11C:
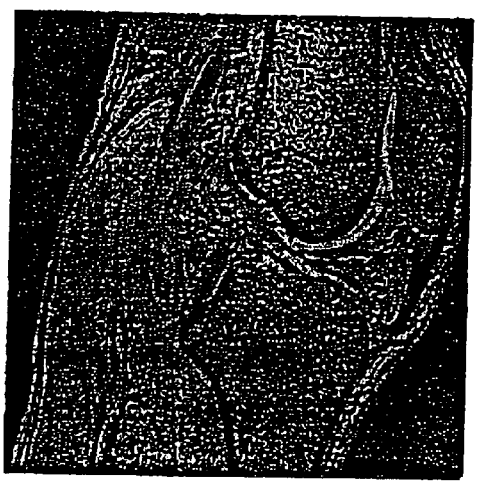
FIGS. 11C and 11D show principal components of the image of FIGS. 11A and 11B.
Figure 11D:
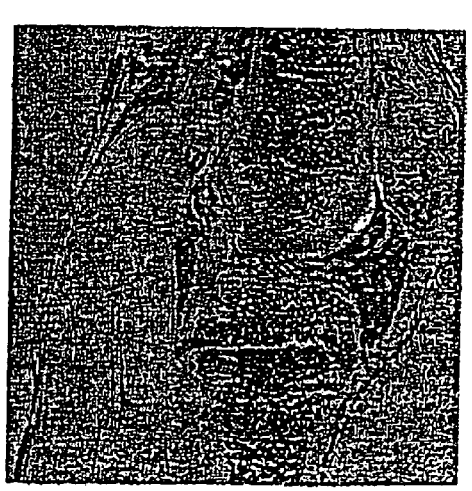

Because $C_x$ is real and symmetric, a set of n orthogonal eigenvectors can be found. Let $e_1$ and $\lambda_i$, i=1, 2, ... N, be the eigenvectors and the corresponding eigenvalues of $C_x$, so that $\lambda_j > \lambda_{j+1}$. Let A be the matrix formed with the eigenvectors of $C_x$. Then the transformation $$y = A(x-m)_x$$

is the discrete K-L transform, and $y_i$, i=1, 2, ... N, are the components of a multispectral image. FIGS. 11C and 11D show the principal components of the two-band spectral image shown in FIGS. 11A and 11B. The advantage of the K-L decomposition of a multispectral image is that the image with the highest contrast is associated with the highest eigenvalue of the correlation matrix, and the image associated with the smallest eigenvalues usually is irrelevant.

The high-contrast, multispectral images thus formed can be utilized for diagnosis and for input to post-processing systems, such as three-dimensional rendering and visualization systems. If the multispectral data are from orthogonal planes or are acquired with some misregistration, the registration and orthogonal fusion steps described herein can be employed to enhance the resolution and contrast.

While a preferred embodiment of the present invention has been set forth above, those skilled in the art who have reviewed the present disclosure will readily appreciate that other embodiments can be realized within the scope of the present invention. For example, while the invention has been disclosed as used with the hardware of FIG. 1, other suitable MRI hardware can be used. For that matter, the invention can be adapted to imaging techniques other than MRI, such as tomography. Also, while the scans are disclosed as being in orthogonal directions, they can be taken in two different but non-orthogonal directions. Therefore, the present invention should be construed as limited only by the appended claims.

What is claimed is:

1. A method of forming an isotropic, high-resolution, three-dimensional diagnostic image of a subject from two-dimensional image data, the method comprising:

(a) scanning the subject with an imaging scanner device, in a first direction relative to the subject, in order to take image data of a first plurality of slices, the image data of the first plurality of slices being two-dimensional image data and having a low resolution in the first direction and a high resolution in directions orthogonal to the first direction;

(b) scanning the subject with said imaging scanner device in a second direction relative to the subject, which is different from the first direction in order to take image data of a second plurality of slices, the image data of the second plurality of slices being two-dimensional image data having at least one dimension substantially in common with the image data of the first plurality of slices and having a low resolution in the second direction and a high resolution in directions orthogonal to the second direction;

(c) registering the first plurality of slices with the second plurality of slices to define a matrix of isotropic, high-resolution voxels in image space, wherein the matrix has unknown high-resolution voxel values; and (d) solving for the unknown high-resolution voxel values in the matrix defined in step (c) in accordance with the image data taken in steps (a) and (b) in order to form the isotropic high-resolution three-dimensional diagnostic image in the image space.

2. The method of claim 1, wherein the second direction is orthogonal to the first direction.

3. The method of claim 1, wherein step (d) comprises treating the image as a linear combination of at least two low-resolution functions and deriving the unknown high-resolution voxel values from the image data of the first and second pluralities of slices.

4. The method of claim 3, wherein the functions are derived through an iterative process using the image data of the first and second pluralities of slices as initial assumptions for the functions.

5. The method of claim 1, wherein step (c) comprises maximizing a correlation based on the directionally scanned image data of the first and second pluralities of slices.

6. The method of claim 5, wherein the correlation is maximized through a hill-climbing technique in which successively larger values of the correlation are located until a local maximum value of the correlation is reached.

7. The method of claim 6, wherein the hill-climbing technique is a multiresolution hill-climbing technique.

8. The method of claim 7, wherein: steps (a) and (b) are performed with an imaging scanner device having an in-plane resolution; and the multiresolution hill-climbing technique is performed with a plurality of resolutions including:
  (i) a maximum resolution which is twice the in-plane resolution; and
  (ii) a minimum resolution which is one-quarter of the in-plane resolution.

9. The method of claim 6, wherein the hill-climbing technique is used to determine both a relative displacement and a relative rotation between the first and second pluralities of slices.

10. A system forming an isotropic, high-resolution, three-dimensional diagnostic image of a subject from two-dimensional image data, the system comprising:
  scanning means for
    (i) scanning the subject in a first direction relative to the subject in order to take image data of a first plurality of slices, the image data of the first plurality of slices being two-dimensional image data and having a low resolution in the first direction and a high resolution in directions orthogonal to the first direction, and
    (ii) scanning the subject in a second direction relative to the subject which is different from the first direction in order to take image data of a second plurality of slices, the image data of the second plurality of slices being two-dimensional image data having at least one dimension substantially in common with the image data of the first plurality of slices and having a low resolution in the second direction and a high resolution in directions orthogonal to the second direction; and
  computing means for
    (i) registering the first plurality of slices with the second plurality of slices in order to define a matrix of isotropic, high-resolution voxels in image space, wherein the matrix has unknown high-resolution voxel values and
    (ii) solving for the unknown high-resolution voxel values in the matrix defined by the computing means in accordance with the image data taken in the first and second directions by the scanning means and thereby form the isotropic, high-resolution, three-dimensional, diagnostic image in the image space.

11. The system of claim 10, wherein the second direction is orthogonal to the first direction.

12. The system of claim 10, wherein the computing means registers the first and second pluralities of slices by maximizing a directionally scanned correlation based on the image data of the first and second pluralities of slices.

13. The system of claim 12, wherein the directionally scanned correlation is maximized through a hill-climbing technique in which successively larger values of the correlation are located until a local maximum value of the correlation is reached.

14. The system of claim 13, wherein the hill-climbing technique is a multiresolution hill-climbing technique.

15. The system of claim 14, wherein:
  the scanning means has an in-plane resolution; and
  the multiresolution hill-climbing technique is performed with a plurality of resolutions including:
    (i) a maximum resolution which is twice the in-plane resolution; and
    (ii) a minimum resolution which is one-quarter of the in-plane resolution.

16. The system of claim 15, wherein the hill-climbing technique is used to determine both a relative displacement and a relative rotation between the first and second pluralities of slices.

17. The system of claim 10, wherein the computing means treats the image as a linear combination of at least two low-resolution functions and deriving the unknown high-resolution voxel values from the image data of the first and second pluralities of slices.

18. The system of claim 17, wherein the functions are derived through an iterative process using the image data of the first and second pluralities of slices as initial assumptions for the functions.

* * * * *